United States Patent [19]

Mune et al.

[11] 4,181,786

[45] Jan. 1, 1980

[54] ANTIBACTERIAL AND ANTIFUNGAL MATERIAL

[75] Inventors: Isao Mune; Keiichi Ushiyama; Kenitiro Saito; Yutaka Moroishi; Tadaichi Nakao, all of Osaka, Japan

[73] Assignee: Nitto Electric Industrial Co., Ltd., Ibaraki, Japan

[21] Appl. No.: 883,988

[22] Filed: Mar. 6, 1978

[30] Foreign Application Priority Data

Mar. 4, 1977 [JP] Japan .................................. 52/24095
Mar. 4, 1977 [JP] Japan .................................. 52/24096

[51] Int. Cl.$^2$ ........................ C08F 20/04; C08F 20/06
[52] U.S. Cl. ............................ 525/327; 260/DIG. 47;
424/14; 424/78; 424/81; 525/328; 525/329
[58] Field of Search ................. 260/DIG. 47; 526/15,
526/14, 16, 240; 424/81, 78, 14

[56] References Cited

U.S. PATENT DOCUMENTS

| | | | |
|---|---|---|---|
| T896055 | 3/1972 | Long | 526/16 |
| 3,322,734 | 5/1967 | Rees | 526/16 |
| 3,647,732 | 3/1972 | Gower et al. | 526/15 |
| 3,789,035 | 1/1974 | Iwami et al. | 526/15 |

FOREIGN PATENT DOCUMENTS 48-23556 7/1973 Japan .
420589 12/1933 United Kingdom ...................... 526/15

*Primary Examiner*—Stanford M. Levin
*Attorney, Agent, or Firm*—Sughrue, Rothwell, Mion, Zinn and Macpeak

[57] ABSTRACT

An antibacterial and antifungal material comprising a polymer containing carboxyl groups in an amount of at least about 0.008 milliequivalent per gram of the polymer and antibacterial and antifungal metallic ions ionically bonded to the carboxyl groups in an amount of at least about 0.0009 millimole per gram of the polymer.

14 Claims, 3 Drawing Figures

ANTIBACTERIAL AND ANTIFUNGAL MATERIAL

BACKGROUND OF THE INVENTION

1. Field of the Invention

This invention relates to an antibacterial and antifungal material comprising a polymer containing carboxyl groups and antibacterial and antifungal metallic ions ionically bonded to the carboxyl groups.

2. Description of the Prior Art

It has been long known that silver ions, copper ions, zinc ions, etc., have antibacterial activity, and salts of these antibacterial ions, for instance, silver nitrate, are used in various fields as a bactericide or disinfectant. However, since an aqueous solution of these ions is used, they are difficult to handle. This limits the scope of their applications. Therefore, attempts have been made to expand the scope of applications of these antibacterial ions and to prolong their effect by reacting them with a polymer containing a polyfunctional group to fix the ions to the polyfunctional group.

Several methods of fixing metallic ions to a polymer are known. For example, Japanese Patent Publication No. 9087/74 discloses an antifouling paint that contains both a copper salt of an unsaturated dicarboxylic acid and metallic copper. As to antibacterial materials per se, those materials in which antibacterial agents are incorporated into a polymer or those materials provided with slow-releasing effect (or sustained-release) have been proposed. However, none of these conventional antibacterial materials have so far proved to exhibit satisfactory effects.

For one thing, Japanese Patent Publication No. 23556/73 discloses a hydrogel comprising a silver complex of a polymer compound which contains both a cyano group and a weakly acidic group. The disclosure is that this complex compound has antibacterial activity but no mention is made as to how long the antibacterial effect lasts. Therefore, testing to evaluate the antibacterial effect of this complex compound has now been conducted and it was found that the complex compound has a sustained effect for a long time and had a high inhibitory effect against bacteria, but the effect of the complex compound in inhibiting the proliferation of true fungi was so low that the proliferation of molds was not fully inhibited.

SUMMARY OF THE INVENTION

Therefore, an object of this invention is to provide a slow-releasing antibacterial and antifungal material that is free from the defects of conventional antibacterial materials, has a high antibacterial and antifungal effect against both bacteria and true fungi, and whose antibacterial and antifungal effect is sustained for a long period of time.

Another object of this invention is to provide an antibacterial and antifungal material having outstanding physical properties such as high chemical resistance, solvent resistance and weather resistance (resistance to discoloration).

The antibacterial and antifungal material of this invention, in one embodiment, comprises a polymer containing carboxyl groups in an amount of at least about 0.008 milliequivalent per gram of the polymer and antibacterial and antifungal metallic ions ionically bonded to the carboxyl groups in an amount of at least about 0.0009 millimole per gram of the polymer.

In a preferred embodiment, the antibacterial and antifungal material of this invention comprises a polymer containing melamine and/or a derivative thereof and carboxyl groups in an amount of at least about 0.008 milliequivalent per gram of the polymer and antibacterial and antifungal metallic ions in an amount of at least about 0.0009 millimole per gram of the polymer ionically bonded to and chelated with the melamine and/or the derivative thereof and the carboxyl groups.

BRIEF DESCRIPTION OF THE DRAWINGS

In FIG. 1 and FIG. 2, curves 1 and 3 represent the film of the antibacterial and antifungal material of this invention immersed in the aqueous peptone solution and in water, respectively, and curves 2 and 4 represent the film of the polymer-silver complex compound immersed in the peptone solution and in water, respectively.

DETAILED DESCRIPTION OF THE INVENTION

Figure 1:
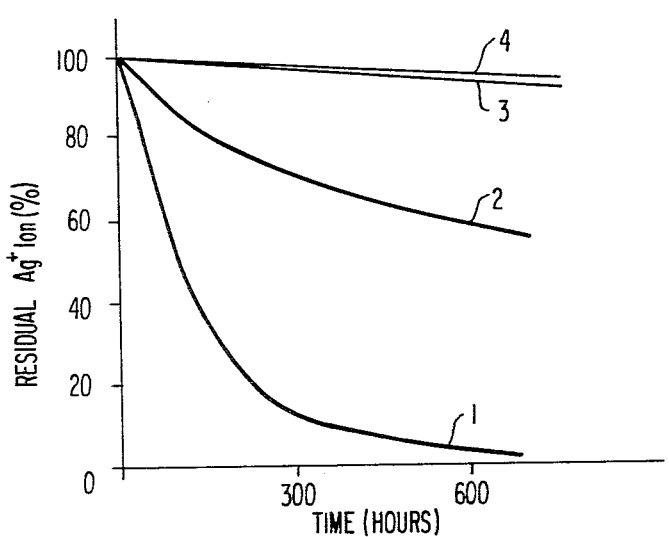
FIG. 1 is a graph showing the time-dependent change of the amount of residual $Ag^+$ ion content in a film of the antibacterial and antifungal material of this invention prepared according to Example 1 given hereinafter and a film of the polymer-silver complex compound disclosed in Japanese Patent Publication No. 23556/73, when they were immersed in a 1% by weight aqueous peptone solution and in water.

The antibacterial and antifungal (hereinafter simply "antibacterial") material of this invention is produced using the following procedures. A polymer is first prepared by polymerizing or copolymerizing one or more monomers containing a carboxyl group, or by copolymerizing one or more such monomers with one or more other monomers copolymerizable therewith. The polymer is then contacted with an antibacterial metallic ion, the excess ion is washed out, and the polymer/ion combination obtained is dried.

Where the antibacterial material of this invention contains melamine or a derivative thereof, the polymer or copolymer or a mixture thereof is then reacted with an antibacterial metallic ion and a melamine compound. In this case, the polymer or copolymer or a mixture thereof may be first reacted with an antibacterial metallic ion to form a salt, and the resulting product is then reacted with the melamine compound. Alternatively, the polymer, copolymer or a mixture thereof may be first reacted with the melamine compound, and the resulting product is then contacted with the antibacterial metallic ion.

Suitable monomers containing a carboxyl group which can be used in this invention can be represented by the general formula (I):

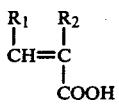

(I)

wherein $R_1$ represents a hydrogen atom, a methyl group or a carboxyl group and $R_2$ represents a hydrogen atom, a methyl group or —$CH_2COOH$; or by the general formula (II):

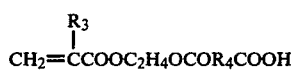

(II)

wherein $R_3$ represents a hydrogen atom or a methyl group and $R_4$ represents —$C_2H_4$—,

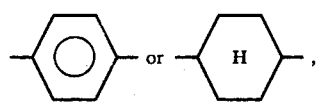

or the acid anhydrides of the compounds of the above general formulae (I) and (II).

Representative examples of the monomers containing a carboxyl group which can be used in this invention include acrylic acid, methacrylic acid, crotonic acid, itaconic acid, maleic acid, methacryloxyethyl acid succinate, methacryloxyethyl acid maleate, methacryloxyethyl acid phthalate, methacryloxyethyl acid hexahydrophthalate, maleic anhydride, itaconic anhydride and the like.

The monomer copolymerizable with the monomer containing a carboxyl group can be freely selected considering the end-use of the antibacterial material according to this invention. However, monomers containing a cyano group, such as acrylonitrile and methacrylonitrile, are not advantageous because, as described above, the resulting product does not have satisfactory antibacterial effects against true fungi. Therefore, it is essential in this invention that the other monomers copolymerizable with the monomer containing a carboxyl group do not contain a cyano. Examples of suitable monomers which can be used in this invention copolymerizable with a monomer containing a carboxyl group are ethylene, propylene, vinyl chloride, vinylidene chloride, vinyl acetate, vinyl propionate, acrylic esters, methacrylic esters, styrene or styrene derivatives, butadiene or butadiene derivatives, acrylamide or acrylamide derivatives, maleic esters, allyl compounds such as allyl propyl esters, vinyl ethers, etc.

The monomers described above may be polymerized using conventional methods such as emulsion polymerization, solution polymerization, and block polymerization, but emulsion polymerization is particularly suitable because particles of the polymer each having many carboxyl groups distributed on the surface of the particles can be produced, which facilitates reaction with the melamine compound and with the antibacterial metallic ions.

Examples of suitable antibacterial metallic ions which can be used in this invention are silver ions, copper ions, and zinc ions, with silver ions being particularly preferred because they have a high antibacterial effect.

In order for the antibacterial material of this invention to exhibit the desired antibacterial effect, the polymer should contain about 0.1 to about 30 wt%, preferably 1 to 10 wt% (i.e., at least about 0.008 milliequivalent of carboxyl groups/gram of polymer, preferably at least about 0.08 milliequivalent of carboxyl groups/gram of polymer) of the monomer containing a carboxyl group and should contain about 0.01 to about 10 wt%, preferably 0.05 to 5 wt% (i.e., at least about 0.0009 millimole of metallic ions/gram of polymer, preferably 0.009 millimole of metallic ions/gram of polymer) of these antibacterial metallic ions based on the total weight of the polymer of the antibacterial material. The antibacterial and antifungal metallic ions are employed in a form of an acid salt thereof which is ion-changeable with the hydrogen atom of a carboxyl group, e.g., an acid salt, such as a nitrate, a sulfate, an acetate, etc. Hydrochloric acid can also be used with copper ion and zinc ion.

Examples of suitable melamine compounds which can be used to produce the antibacterial material of this invention when such contains melamine or a derivative thereof include melamine or a derivative thereof. Suitable melamine compounds which can be used in this invention are represented by the general formula (III):

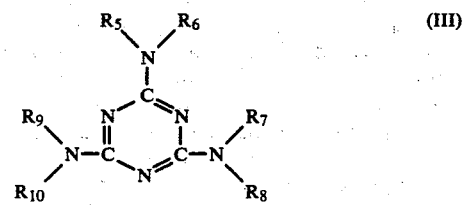

(III)

wherein $R_5$ to $R_{10}$, which may be the same or different, each represents a hydrogen atom, —$CH_2OH$ or —$CH_2OC_nH_{2n+1}$ and wherein n is an integer of 1 to 4. Specific examples include polymethylol melamines such as mono-, di-, tri-, tetra-, penta- or hexa-methylol melamine, and alkylated methylol melamines such as methylated methylol melamine or butylated methylol melamine. These melamine compounds can be used in the form of a solution or an emulsion. A suitable concentration for the melamine compounds is about 1 to about 80 wt%, preferably about 5 to about 80 wt%, of the solution or the emulsion.

These melamine compounds, when subjected to thermal reaction, form a chemical bonding not only with the antibacterial metallic ion but also with the carboxyl group. The reaction with the carboxyl group generally results in the formation of melamine cross-linking through which the melamine compound is firmly fixed in the resulting polymer. On the other hand, the melamine compound will itself undergo a self-condensation becoming polymeric in the course of the reaction with the antibacterial metallic ion and with the carboxyl group. A suitable temperature for the incorporation of the melamine compound is about 80° to about 180° C., preferably about 100° to about 160° C. Catalysts are not essential, but, if the temperature is low, a catalyst can be used to accelerate the reaction. Representative examples of the catalysts which can be used include carboxylic acid esters such as dimethyl oxalate, amine hydrochlorides such as ethylamine hydrochloride or triethanolamine hydrochloride, organic halogen compounds such as α,α'-dichlorohydrin, acid anhydrides such as maleic anhydride or phthalic anhydride, and the like. The amount of the catalyst which can be used is about 0.1 to about 5% by weight, preferably about 0.5 to about 3% by weight, based on the weight of the melamine compound. A suitable reaction time ranges from about 1 to about 30 minutes, preferably about 2 to about 5 minutes.

A second method which can be used for producing the antibacterial material of this invention comprises contacting a carboxyl group-containing monomer with an antibacterial metallic ion to ionically bond the carboxyl group and the metallic ion, and then polymerize or copolymerize such a monomer in the same manner as described above. Where melamine or a derivative thereof is present in the polymer, the polymer or copolymer can then be reacted with the melamine compound described above.

A third method comprises polymerizing a carboxyl group-containing monomer to form an oligomer whose degree of polymerization is about 5 to about 100, introduce an antibacterial metallic ion into the oligomer, and then further polymerize using a suitable cross-linking agent such as a polyisocyanate compound, a peroxide, an aziridine compound, or the like.

Another possible method which can be used is to first prepare a polymer or copolymer by polymerizing or copolymerizing a carboxyl group-containing monomer in the same manner as described above, form the polymer or copolymer into a porous solidified product, a film, a fiber and other formed articles using conventional methods, and then contact such formed articles with an antibacterial metallic ion. Where the melamine compound is to be reacted, such can be reacted with the material after contact with the antibacterial metallic ion or the opposite order can be used.

The antibacterial material of this invention may also be produced, as described in, for example, T. Matsumoto et al., *Kobunshi Ronbunshu*, 31, pages 112–118 (1974), by first preparing a polymer or copolymer of an ester such as an acrylic ester or a methacrylic ester, converting the functional group present into a carboxyl group by an after-treatment such as saponification, and contacting the carboxyl group-containing polymer or copolymer with an antibacterial metallic ion and, then with the melamine compound. This method is particularly advantageous when emulsion polymerization is utilized as the polymerization method.

Still another method which can be used, as described in, for example, M. Shimpo, *Nippon Setchaku Kyokaishi*, 6, page 327 (1970), comprises first exposing polymers such as diene compounds or polyolefins that do not contain a carboxyl group to oxygen, heat, light, etc., so as to cause an auto-oxidation thereof to occur and then introducing carboxyl groups at the terminals or side chains, and subsequently combining the carboxyl group-containing polymer with an antibacterial metallic ion and with a melamine compound, if such is to be used.

Any one of these methods can be used to produce an antibacterial material containing a carboxyl group and an antibacterial metallic ion ionically bonded to the carboxyl group. All of the carboxyl groups present do not have to be bonded to a metallic ion. It is sufficient if the metallic ion is present in the polymer in the amount described herein. The thus-produced antibacterial material can be blended with suitable additives at any stage of subsequent processing before the material is shaped into a formed article such as a film. The antibacterial effect of the final product according to this invention is sustained for a long period and a high antibacterial effect is exhibited both against bacteria and true fungi.

In order for the antibacterial material of the second embodiment of this invention to exhibit the desired antibacterial effect, it should contain about 0.1 to about 30 wt%, preferably 1 to 10 wt% (i.e., at least about 0.008 milliequivalent of carboxyl groups/gram of polymer, preferably at least about 0.08 milliequivalent of carboxyl groups/gram of polymer), of the monomer containing a carboxyl group and about 0.1 to about 50 wt%, preferably 2 to 10 wt% of the melamine compound and, as described above, about 0.01 to about 10 wt%, preferably 0.05 to 5 wt% (i.e., at least about 0.0009 millimole of metallic ions/gram of polymer, preferably 0.009 millimole of metallic ions/gram of polymer), of antibacterial metallic ion such as $Ag^+$ ion.

In bonding the antibacterial and antifungal metallic ions to a preformed polymer containing carboxyl groups, a suitable temperature range for the bonding is about 10° to about 80° C., preferably about 20° to about 60° C. The higher the temperature is, the smoother the bonding of the metallic ions is. However, if the temperature is too high, heat distortion of polymers can occur (i.e., a temperature lower than the glass transition temperature is desirable). Therefore, a temperature of around 30° C. is especially preferred for use. In bonding the antibacterial and antifungal metallic ions to a monomer containing a carboxyl group which is then to be polymerized, a suitable temperature range for the bonding is about 0° to about 50° C., preferably about 0° to about 30° C. Since heat is generated by the bonding, it is necessary to conduct the bonding of the antibacterial and antifungal metallic ions at a relatively low temperature. In bonding the antibacterial and antifungal metallic ions, an aqueous solution, e.g., of a concentration of about 1 wt% to a saturation concentration, preferably about 3 to about 20 wt%, of the metallic ions is employed. A suitable contact time for the bonding will vary depending on the material to which the ions are to be bonded, but, in general, for bonding to a monomer containing a carboxyl group, about 1 minute to about 1 hour, preferably about 2 to about 30 minutes, is suitable and for bonding to a preformed polymer containing carboxyl groups, about 1 minute to about 2 hours, preferably about 5 minutes to about 1 hour, is suitable.

The antibacterial material of this invention thus-produced exhibits a high antibacterial effect both against bacteria and true fungi, and the antibacterial effect is sustained for a long time. In addition, in the preferred embodiment of this invention, introduction of the melamine cross-linking by heat treatment at a temperature higher than about 100° C. provides the antibacterial material with improved physical properties such as high solvent resistance and high strength.

A further advantage of the antibacterial material of this invention that contains silver ions as the antibacterial metallic ion is that the antibacterial material is resistant to oxidation (therefore, discoloration) due to exposure to light, and this is an outstanding improvement over conventional products.

To show the effect of the antibacterial material of this invention, the following evaluations were conducted on a film of the antibacterial material of this invention prepared according to Example 1 and Example 5 (described hereinafter) which had silver ions fixed to carboxyl groups and, as a control film, a film prepared from the copolymer-silver complex compound disclosed in Japanese Patent Publication No. 23556/73 wherein silver ions were fixed to carboxyl groups and cyano groups. In these tests, the content of fixed $Ag^+$ ion was controlled such that it was constant.

(I) Disc Method Evaluation of Antibacterial Effect

Bacteria and true fungi used: *Bacillus subtilis, Staphylococcus aureus, Escherichia coli, Pseudomonas aeruginosa, Candida albicans, Aspergillus niger, Chaetomium glabosum, Cladosporium resinae, Penicillium citrinum,* and *Trichoderma sp.*

Each of the test films was placed on a meat extract-agar plate inoculated with $10^5$ to $10^6$ bacterial cells, and incubation was continued overnight at 37° C. to observe if an inhibition zone was formed.

The two test films were also placed on a potato-sucrose-agar plate inoculated with about $10^5$ true fungi spores, and incubation was continued at 30° C. for a week to observe if any inhibition zone was formed.

Table 1 shows the results obtained in these tests.

Table 1

| | Film | | |
|---|---|---|---|
| Bacteria and True Fungi Used | Example 1 Film $COO^-...Ag^+$ | Example 5 Film $COO^-...Ag^+...$Melamine | Control Film $COO^-...Ag^+...CN$ |
| *Bacillus subtilus* | o | o | o |
| *Staphylococcus aureus* | o | o | o |
| *Escherichia coli* | o | o | o |
| *Pseudomonas aeruginosa* | o | o | o |
| *Candina albicans* | o | o | o |
| *Aspergillus niger* | o | o | x |
| *Chaetomium glabosum* | o | o | x |
| *Cladosporium resinae* | o | o | x |
| *Penicillium citrinum* | o | o | x |
| *Trichoderma sp.* | o | o | x | o: inhibition zone formed.
x: no inhibition zone formed.

(II) Mortality of Fungi on the Films

Each test film was coated with 0.1 ml of a suspension of $10^4$ to $10^5$ spores of *Aspergillus flavus* in a 0.005% by weight aqueous solution of sodium dodecylbenzenesulfonate, stored at 30° C. for 24 hours, subjected to sampling dilution, inoculated on a Sabouraud plate, and incubated at 30° C. for 24 hours. The number of surviving spores was counted to determine the mortality. Table 2 shows the results obtained in this test.

Table 2

| Film | Mortality (%) |
|---|---|
| Example 1 Film | 99 |
| Example 4 Film | 99 |
| Control Film | 0 |

(III) Chemical Resistance

Each test film was immersed in each of the chemicals listed in Table 3 below at 22° C. for 48 hours. Using *Escherichia coli*, the antibacterial effect of each film was evaluated in accordance with the disc method. Table 3 shows the results obtained in this evaluation.

Table 3

| | Film | | |
|---|---|---|---|
| Chemical Solution | Example 1 Film | Example 5 Film | Control Film |
| 1N-HCl | x | o | x |
| $1N-HNO_3$ | x | o | x |
| 1N-NaOH | o | o | o |
| $5\%-H_2O_2$ | o | o | o |
| $5\%-KHSO_3$ | o | o | o |
| $5\%-NaClO_3$ | o | o | o |

(IV) Sustainability of Antibacterial Effect

Each film was immersed in still water (replaced every 12 hours), running water and boiling water (replaced every 12 hours) until the antibacterial effect of the film was shown to no longer be present employing the disc method using *Escherichia coli*. Table 4 shows the period of time the antibacterial effect of the test films was sustained.

Table 4

| | Film | | |
|---|---|---|---|
| | Example 1 Film | Example 5 Film | Control Film |
| Still Water | >1 year | >1 year | >1 year |
| Running Water | >1 year | >1 year | >1 year |
| Boiling Water | 6 months | 6 months | 6 months |

(V) Discoloration

The degree of discoloration of each film was determined by leaving the films outdoors and by irradiating the films with a weatherometer (Standard Weather Meter WE-T-2NHC Type, manufactured by Suga Shikenki K.K.). Table 5 shows the results obtained in this test.

Table 5

| | Film | | |
|---|---|---|---|
| | Example 1 Film | Example 5 Film | Control Film |
| Outdoors | | | |
| 2 Days | o | o | o |
| 7 Days | o | o | x |

Table 5-continued

| | Film | | |
|---|---|---|---|
| | Example 1 Film | Example 5 Film | Control Film |
| 30 Days Weatherometer | Δ | o | x |
| 24 Hours | Δ | o | x | o: No discoloration
Δ: Slight discoloration
x: Discoloration ranging from brown to purple The results in these tables show that the antibacterial material of this invention is equal to the cyano group-containing silver complex compound with respect to chemical resistance and sustainability of antibacterial effect, but the antibacterial effect against true fungi and the ability to kill true fungi on a film of the antibacterial material of this invention are greater than those of the control.

While not desiring to be bound, it is presumed that this phenomenon can be explained by reference to FIG. 1 and FIG. 2.

Figure 2:
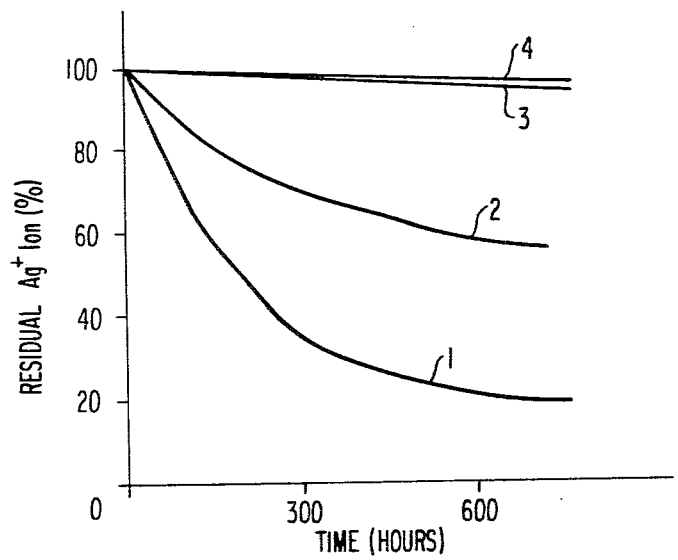
FIG. 2 is a graph showing the time-dependent change of residual $Ag^+$ ion content in a film of the antibacterial and antifungal material of this invention prepared according to Example 5 given hereinafter and a film of the polymer-silver complex compound disclosed in Japanese Patent Publication No. 23556/73, when they were immersed in water and in a 1% by weight aqueous peptone solution.

FIG. 1 and FIG. 2 show the amount of residual $Ag^+$ ions present in the film of the antibacterial material of this invention prepared in Example 1 and prepared in Example 5, respectively, along with a control film prepared from a copolymer-silver complex compound as disclosed in Japanese Patent Publication No. 23556/73 having silver ions fixed to carboxyl groups and cyano groups that were each immersed for a certain period in water and in 1% by weight peptone aqueous solution. The amount of residual $Ag^+$ ions was determined by measuring the $Ag^+$ ion content in the water or the 1% by weight aqueous peptone solution using atomic-absorption spectroscopic analysis. In FIG. 1 and FIG. 2, curves 1 and 2 represent the film of the antibacterial material of this invention and the control film, respectively, immersed in the 1% by weight aqueous peptone solution. Curves 3 and 4 represent the film of the antibacterial material of this invention and the control film, respectively, immersed in water.

The curves in FIGS. 1 and 2 clearly show that the films of the antibacterial material of this invention and the control film release $Ag^+$ ions into water at a substantially equal rate, but in the 1% by weight aqueous peptone solution, both embodiments of the films of the antibacterial material of this invention release the $Ag^+$ ions faster than the control film. In other words, under circumstances where a nutrient source such as peptone exists or where conditions favorable to bacterial or fungal proliferation exist, the rate of release of $Ag^+$ ions from the antibacterial material of this invention increases, which presumably exhibits an inhibitory action against bacteria and true fungi.

Therefore, the antibacterial effect of the antibacterial material according to this invention is not only sustained for a long period, but also the desired effect is exhibited when required.

The preferred embodiment of the antibacterial material of this invention is particularly advantageous in that the rate at which the antibacterial material releases silver ions can be controlled by appropriately changing the content of the melamine compound.

Figure 3:
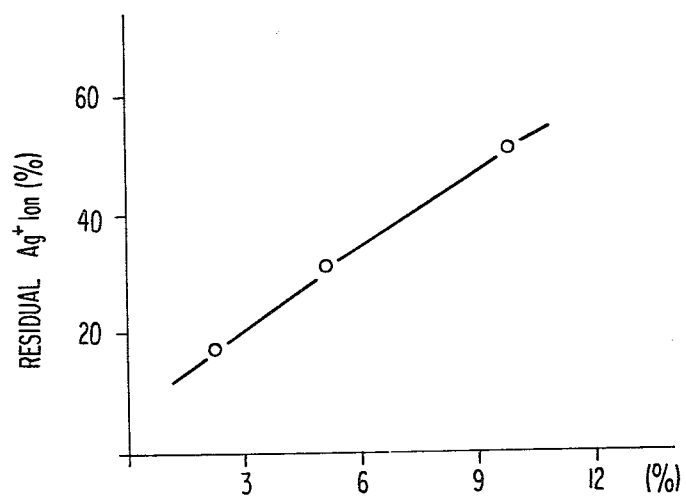
FIG. 3 is a graph showing the relationship between the residual $Ag^+$ ion content and the melamine compound content after a film of the antibacterial and antifungal material of this invention produced as described in Example 5 was immersed in a 1% aqueous peptone solution for 300 hours.

FIG. 3 shows the relationship between the residual silver ion content and the amount of the melamine compound (solid content) present in the film of the antibacterial material prepared in Example 5 (described hereinafter) having silver ions fixed to the carboxyl groups and the melamine compound. FIG. 3 shows the results obtained after the film was immersed in a 1% aqueous peptone solution for 300 hours, which results clearly show that the residual silver ion content is proportional to the amount of the melamine compound (solid content) used. It is, therefore, possible for the sustained-release of antibacterial metallic ions from the antibacterial material of this invention to be controlled by simply changing the amount of the melamine compound depending upon the kind of bacteria or true fungi and the form in which the antibacterial material of this invention is employed.

As described before, this embodiment of the antibacterial material of this invention is ordinarily produced by first producing a polymer containing a carboxyl group and reacting the polymer produced with the melamine compound before or after introducing the antibacterial metallic ion into the polymer. On the other hand, the polymer-silver complex compound described in Japanese Patent Publication No. 23556/73 uses a monomer containing a cyano group as the constituent of the polymer, and so, the amount of the monomer that can be used is limited by polymerizability or the ratio of conversion to a copolymer, or if it can be varied, sustained-release is not controllable over a wide range. This antibacterial material of this invention is substantially free from this defect of the prior art materials, and a minimum change in the content of the melamine compound gives rise to a great change in the sustained-release characteristics.

Another advantage of the film of the antibacterial material according to this invention is that it is more resistant to discoloration than the control film. It can, therefore, be used in many applications where discoloration is not desired, such as building wall paints, wallpapers for use in homes, bedcovers or sheets for use in hospitals, etc.

The antibacterial material of this invention having the advantages described above may be either used per se in the form of a liquid, an emulsion, a suspension, a paste, a powder, particles, a sheet, a film, formed articles, porous solidified products (including porous films) and fibers, or used with carriers such as non-woven fabrics, foamed sheets, papers, synthetic resin films and inorganic sheets. In either way, the antibacterial material of this invention may be used as various coating compositions such as marine paints and building wall paints, filter media, ion exchangers, dialysis membranes, anti-slime agents for pulp slurries, air filters, wallpapers, antibacterial clothes, packaging materials, bedcovers and sheets for use in hospitals, and liners for clothes cabinets, closets and cupboards.

In addition, the high chemical resistance, the high strength and the high stability against light allow the antibacterial material of this invention to be used under more severe conditions than those under which the conventional antibacterial material can be used.

This invention is described in greater detail by reference to the following examples, but this invention is not to be construed as being limited to these examples. Unless otherwise specified, all parts and percentages are by weight.

EXAMPLE 1

A dispersion of 100 parts of a monomer mixture of 50% styrene, 40% ethyl acrylate, 9% acrylic acid and 1% divinyl benzene in 150 parts of water containing 0.5% ammonium persulfate and 5% of an emulsifying agent ("Noigen EA 160" manufactured by Dai-ichi Kogyo Seiyaku) was stirred in a nitrogen atmosphere to initiate polymerization at 70° C. The system was maintained at about 75° C. for 5 hours to complete the polymerization. After the polymerization, the solid material was separated to obtain a uniform emulsion having a non-volatile solid content of 40% and an average particle size of 0.08μ.

The emulsion was flow-cast on a glass plate, immediately immersed for 5 minutes in a liquid medium (water:methyl ethyl ketone weight ratio: 7:3) with 5% hydrochloric acid dissolved therein to obtain a porous solid product, the particles of which were partially bonded. The solid product was immersed in pure water to replace the absorbed medium with water until equilibrium was reached, separated from the glass plate, washed with water, and dried.

The porous solid product obtained was immersed in a 5% aqueous AgNO$_3$ solution for 20 minutes, thoroughly washed with water, dried to produce an antibacterial porous film having Ag$^+$ ions fixed to the carboxyl groups. Various characteristics of the film were evaluated in accordance with the method defined hereinbefore. The film exhibited a high antibacterial effect against various kinds of bacteria and true fungi, and the antibacterial effect was sustained for more than 6 months in boiling water. A porous film of this type can be used per se as a medium for filtering water contaminated with bacteria or true fungi, or as an air filter. The film may also be used after being reinforced with carriers such as a non-woven fabric.

The porous antibacterial film was then processed into a uniform film by heating at 140° C. under atmospheric pressure for 3 minutes. The results of the evaluation of the characteristic of this film were as described hereinbefore. The film can be used for wallpapers, bedcovers and sheets.

EXAMPLE 2

A monomer mixture of 55% styrene, 35% butyl acrylate, 6% methacrylic acid and 4% acrylic acid/silver salt monomer was subjected to emulsion polymerization using the same method as described in Example 1. A synthetic resin emulsion having a non-volatile solid content of 45% and an average particle size of 0.09μ was obtained.

The emulsion was flow-cast on a polyester film and dried at 80° C. for 3 minutes to obtain a uniform film. When this film was evaluated in the same manner as described in Example 1, equally good results were obtained. The antibacterial synthetic resin emulsion produced in Example 2 can be used as various coating compositions such as marine paints and building wall paints. If the resin is processed into a film, the film can be used in wallpapers, bedcovers, etc. If the resin is processed into fibers, the fibers can be used to make antibacterial clothes.

EXAMPLE 3

A dispersion of 100 parts of a monomer mixture of 40% styrene, 50% ethyl acrylate and 10% acrylic acid in 200 parts of toluene was mixed with 0.5% of 4,4-azobisisobutyronitrile, and polymerized at 70° C. in a nitrogen atmosphere for 7 hours.

The polymer solution obtained was flow-cast on a polyester film and dried at 70° C. for 3 minutes to obtain a uniform film.

The film was immersed in a 1 N NaOH aqueous solution for 20 minutes and thoroughly washed with water. The film was then immersed in a 5% aqueous AgNO$_3$ solution for 20 minutes, washed with water, and dried. The film thus-obtained was evaluated as described in Example 1, and equally good results were obtained.

EXAMPLE 4

A dispersion of 100 parts of a monomer mixture of 50% styrene, 40% ethyl acrylate, 9% acrylic acid and 1% divinyl benzene in 150 parts of water containing 0.5% ammonium persulfate and 5% of an emulsifying agent ("Noigen EA 160" manufactured by Dai-Ichi Kogyo Seiyaku) was stirred in a nitrogen atmosphere to initiate polymerization at 70° C. The system was maintained at about 75° C. for 5 hours to complete the polymerization. After the polymerization, the solid material was separated to obtain a uniform emulsion having a non-volatile solid content of 40% and an average particle size of 0.08μ.

The emulsion was flow-cast on a glass plate, immediately immersed for 5 minutes in a liquid medium (water:methyl ethyl ketone weight ratio: 7:3) with 5% hydrochloric acid dissolved therein to obtain a porous solid product, the particles of which were partially bonded. The solid product was immersed in pure water to replace the absorbed medium with water until equilibrium was reached, separated from the glass plate, washed with water, and dried.

The porous solid product thus-obtained was immersed in a 5% aqueous AgNO$_3$ solution for 20 minutes, thoroughly washed with water and dried to obtain a solid product. The product was immersed in a 5% aqueous hexamethylol melamine solution and heated at 130° C. for 3 minutes to introduce a [COO$^-$ . . . Ag$^+$ . . . melamine] linkage. The porous antibacterial material thus-produced exhibited a high antibacterial effect against various bacteria and true fungi, whose antibacterial effect was sustained for a long time, had high chemical resistance, and was entirely free from discoloration due to exposure to light. This porous material can be used per se as a medium for filtering water contaminated with bacteria or true fungi or as an air filter. This material may also be used after reinforcing with carriers such as a non-woven fabric.

EXAMPLE 5

A monomer mixture of 55% styrene, 35% butyl acrylate, 6% methacrylic acid and 4% acrylic acid/silver salt monomer was subjected to emulsion polymerization using the same method as described in Example 4. A synthetic resin emulsion having a non-volatile solid content of 45% and an average particle size of 0.09μ was obtained.

A mixture of 100 parts of the emulsion and 5 parts of a 70% aqueous hexamethylol melamine solution was flow-cast on a polyester film and dried at 130° C. for 3 minutes to obtain a uniform film. The characteristics of this film were evaluated in the manner described hereinbefore.

Several films were prepared by repeating the procedures of Example 5 except that the parts of the aqueous hexamethylol melamine solution were varied, and the films were immersed in a 1% aqueous peptone solution for 300 hours. FIG. 3 shows the relationship between the residual Ag$^+$ ion content and the amount of the hexamethylol melamine used.

EXAMPLE 6

A monomer mixture of 40% methyl methacrylate, 50% ethyl acrylate, 6% acrylic acid, and 4% acrylic acid/copper salt monomer was subjected to emulsion polymerization in the same manner as described in Example 4. A synthetic resin emulsion having a non-volatile solid content of 44% and an average particle size of 0.09μ was obtained.

A mixture of 100 parts of the emulsion and 10 parts of a butylated methylol melamine emulsion (solid content: 35%) was flow-cast on a polyester film and dried at 145° C. for 3 minutes to obtain a uniform film. Similar to the film obtained in Example 5, this film exhibited high antibacterial effects against various bacteria and true fungi, had high chemical resistance, and its antibacterial effect lasted for a long time. This film is particularly suitable for use as a marine antifouling coating.

EXAMPLE 7

A mixture of 100 parts of the emulsion prepared in Example 4, 7 parts of an 80% aqueous trimethylol melamine solution and 0.1 part of 2-amino-methylpropanol-1-hydrochloride (catalyst) was flow-cast on a polyester film and dried at 110° C. for 3 minutes to obtain a uniform film. The film was immersed in a 10% aqueous AgNO$_3$ solution for 20 minutes, thoroughly washed with water and dried to obtain an antibacterial film. Similar to the film prepared in Example 5, this film had a high antibacterial effect and chemical resistance, and the antibacterial effect was sustained for a long time, and it was entirely free from discoloration due to light. This film is suitable for use, for example, as a packaging material and a wallpaper.

EXAMPLE 8

A monomer mixture of 60% methyl methacrylate, 40% butyl acrylate, 5% acrylic acid and 5% acrylic acid/zinc salt monomer was subjected to emulsion polymerization in the same manner as described in Example 4 to obtain a synthetic resin emulsion having a non-voatile solid content of 44% and an average particle size of 0.1μ.

A mixture of 100 parts of the emulsion and 5 parts of a 50% hexamethylol melamine aqueous solution was flow-cast onto a polyester film and dried at 140° C. for 3 minutes to obtain a uniform film. Similar to the film obtained in Example 5, this film exhibited high antibacterial and antifungal effects against various bacteria and true fungi, the antibacterial and antifungal effect lasting for a long time, and the film was resistant to chemicals.

While the invention has been described in detail and with reference to specific embodiments thereof, it will be apparent to one skilled in the art that various changes and modifications can be made therein without departing from the spirit and scope thereof.

What is claimed is:

1. An antibacterial and antifungal material comprising a polymer containing carboxyl groups, but not containing any cyano groups, in an amount of at least about 0.008 milliequivalent per gram of said polymer and silver ions ionically bonded to said carboxyl groups in an amount of at least about 0.0009 millimole per gram of said polymer.

2. The antibacterial and antifungal material of claim 1, wherein said polymer is a polymer of a monomer containing a carboxyl group represented by the general formula (I):

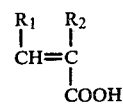

wherein R$_1$ represents a hydrogen atom, a methyl group or a carboxyl group and R$_2$ represents a hydrogen atom, a methyl group or —CH$_2$COOH; or by the general formula (II):

wherein R$_3$ represents a hydrogen atom or a methyl group and R$_4$ represents —C$_2$H$_4$—,

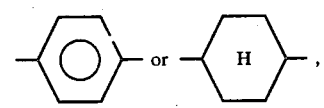

or the acid anhydrides of the compounds of the above general formulae (I) and (II).

3. The antibacterial and antifungal material of claim 2, wherein said monomer containing a carboxyl group is acrylic acid, methacrylic acid, crotonic acid, itaconic acid, maleic acid, methacryloxyethyl acid succinate, methacryloxyethyl acid maleate, methacryloxyethyl acid phthalate, methacryloxyethyl acid hexahydrophthalate, maleic anhydride or itaconic anhydride.

4. The antibacterial and antifungal material of claim 2, wherein said polymer comprises a polymer of an addition polymerizable monomer containing a carboxyl group with another addition polymerizable monomer not containing a carboxyl group or a cyano group.

5. The antibacterial and antifungal material of claim 4, wherein said addition polymerizable monomer not containing a carboxyl group or a cyano group is selected from the group consisting of ethylene, propylene, vinyl chloride, vinylidene chloride, vinyl acetate, vinyl propionate, an acrylic ester, an addition polymerizable monomer containing a styrene moiety, an addition polymerizable monomer containing a butadiene, moiety, an addition polymerizable monomer containing an acrylamide moiety, a maleic ester, an allyl compound and a vinyl ether.

6. The silver of claim 1, wherein the antibacterial and antifungal metallic ions are present in an amount of about 0.01 to about 10% by weight based on the total weight of said polymer.

7. The antibacterial and antifungal material of claim 2, wherein said monomer containing a carboxyl group is present in said polymer in an amount of about 0.1 to about 30% by weight based on the total weight of said polymer.

8. The antibacterial and antifungal material of claim 1, wherein said polymer additionally contains melamine and/or a derivative thereof represented by the general formula (III):

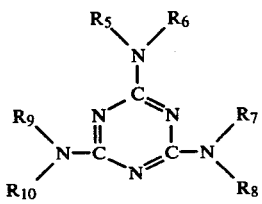

(III)

wherein $R_5$ to $R_{10}$, which may be the same or different, each represents a hydrogen atom, —$CH_2OH$ or —$CH_2OC_nH_{2n+1}$ and wherein n is an integer of 1 to 4 and said silver ions are ionically bonded to and chelated with said melamine and/or said derivative thereof and said carboxyl groups.

9. The antibacterial and antifungal material of claim 8, wherein said polymer is a polymer of a monomer containing a carboxyl group represented by the general formula (I):

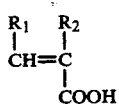

(I)

wherein $R_1$ represents a hydrogen atom, a methyl group or a carboxyl group and $R_2$ represents a hydrogen atom, a methyl group or —$CH_2COOH$; or by the general formula (II):

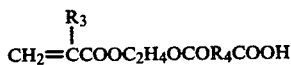

(II)

wherein $R_3$ represents a hydrogen atom or a methyl group and $R_4$ represents —$C_2H_4$—,

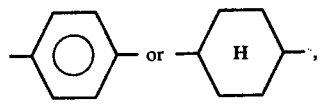

or the acid anhydrides of the compounds of the above general formulae (I) and (II).

10. The antibacterial and antifungal material of claim 9, wherein said monomer containing a carboxyl group is acrylic acid, methacrylic acid, crotonic acid, itaconic acid, maleic acid, methacryloxyethyl acid succinate, methacryloxyethyl acid maleate, methacryloxyethyl acid phthalate, methacryloxyethyl acid hexahydrophthalate, maleic anhydride or itaconic anhydride.

11. The antibacterial and antifungal material of claim 9, wherein said polymer comprises a polymer of an addition polymerizable monomer containing a carboxyl group with another addition polymerizable monomer not containing a carboxyl group or a cyano group.

12. The antibacterial and antifungal material of claim 8, wherein said polymer contains said monomer containing said carboxyl group in an amount of about 0.1 to about 30% by weight, said melamine and/or said derivative thereof in an amount of about 0.1 to about 50% by weight and said silver ions in an amount of about 0.01 to about 10% by weight, each based on the total weight of said polymer.

13. The antibacterial and antifungal material of claim 1, wherein said material is in the form of a film, a sheet or a fiber.

14. The antibacterial and antifungal material of claim 8, wherein said material is in the form of a film, a sheet or a fiber.

* * * * *